(12) United States Patent
Liu

(10) Patent No.: US 11,039,090 B2
(45) Date of Patent: Jun. 15, 2021

(54) MULTIPURPOSE IMAGING AND DISPLAY SYSTEM

(71) Applicant: Yang Liu, Akron, OH (US)

(72) Inventor: Yang Liu, Akron, OH (US)

(73) Assignee: The University of Akron, Akron, OH (US)

(*) Notice: Subject to any disclaimer, the term of this patent is extended or adjusted under 35 U.S.C. 154(b) by 0 days.

(21) Appl. No.: 16/599,850

(22) Filed: Oct. 11, 2019

(65) Prior Publication Data

US 2020/0053298 A1 Feb. 13, 2020

Related U.S. Application Data

(63) Continuation of application No. 15/031,791, filed as application No. PCT/US2014/062454 on Oct. 27, 2014, now Pat. No. 10,447,947.

(60) Provisional application No. 61/895,630, filed on Oct. 25, 2013.

(51) Int. Cl.
| | |
|---|---|
| *H04N 5/33* | (2006.01) |
| *H04N 13/204* | (2018.01) |
| *A61B 5/00* | (2006.01) |
| *A61B 5/0205* | (2006.01) |
| *A61B 5/1455* | (2006.01) |
| *G02B 27/01* | (2006.01) |
| *H04N 7/15* | (2006.01) |

(52) U.S. Cl.
CPC .......... *H04N 5/332* (2013.01); *A61B 5/0059* (2013.01); *A61B 5/0077* (2013.01); *A61B 5/02055* (2013.01); *A61B 5/14552* (2013.01); *A61B 5/7445* (2013.01); *G02B 27/0172* (2013.01); *H04N 7/15* (2013.01); *H04N 13/204* (2018.05); *A61B 5/0002* (2013.01); *A61B 5/0071* (2013.01); *G02B 2027/0138* (2013.01)

(58) Field of Classification Search
CPC combination set(s) only.
See application file for complete search history.

(56) References Cited

U.S. PATENT DOCUMENTS

| | | | |
|---|---|---|---|
| 2005/0033145 A1* | 2/2005 | Graham | A61B 5/0071 600/407 |
| 2006/0181482 A1* | 8/2006 | Iaquinto | A61B 90/36 345/8 |

(Continued)

*Primary Examiner* — Phung-Hoang J Nguyen
(74) *Attorney, Agent, or Firm* — Renner Kenner Greive Bobak Taylor & Weber

(57) ABSTRACT

A multi-purpose imaging and display system includes a display; a detector coupled to the display and having a field of view; and a filter communicating with the detector. The field of view is imaged by the detector through the filter, the filter configured to be sensitive to a first frequency spectrum, so the detector displays only objects within the field of view on the detector that emit one or more frequencies within the first frequency spectrum. The detector and filter can work together in different operational states or modes for acquiring image data of a target object under investigation. A computing device can be included to process acquired image data, and communication interfaces can be employed to achieve networking of multiple systems. A peripheral interface allows a plurality of peripheral devices to be selectively added to tailor the data acquisition and display capabilities of the imaging and display system.

17 Claims, 6 Drawing Sheets

(56) References Cited

U.S. PATENT DOCUMENTS

| | | | | |
|---|---|---|---|---|
| 2008/0129844 A1* | 6/2008 | Cusack | ............... | H04N 5/232 348/241 |
| 2010/0117960 A1* | 5/2010 | Huntzicker | ........... | G06F 1/1626 345/158 |
| 2010/0283842 A1* | 11/2010 | Guissin | ............... | G02B 13/06 348/68 |
| 2011/0122231 A1* | 5/2011 | Fujieda | ................ | G06T 7/75 348/47 |
| 2012/0289777 A1* | 11/2012 | Chopra | ............ | A61B 5/02028 600/109 |
| 2013/0229509 A1* | 9/2013 | Kim | ................ | G01B 11/2513 348/86 |

\* cited by examiner

MULTIPURPOSE IMAGING AND DISPLAY SYSTEM

CROSS-REFERENCE TO RELATED APPLICATIONS

This application is a continuation of U.S. patent application Ser. No. 15/031,791 filed on Apr. 25, 2016, which is a 35 U.S.C. 371 filing of PCT/US2014/062454 filed Oct. 27, 2014, which claims the benefit of U.S. Provisional Application No. 61/895,630 filed on Oct. 25, 2013, the contents of which is incorporated herein by reference.

TECHNICAL FIELD

The present invention generally relates to imaging and display systems. Particularly, the present invention relates to a multipurpose imaging and display system having a detector capable of being selectively converted from one imaging mode to another to image various target frequencies in order to acquire image data for viewing on a wearable display. More particularly, the present invention relates to a multi-purpose imaging and display system having a wearable display and a multi-mode detector, which provides a network communication link with other imaging and display systems to facilitate collaborative communication, and that provides a communication link with various specialized data acquisition peripherals for attachment to the display to customize the data acquisition and display features of the system.

BACKGROUND OF THE INVENTION

Due to the continued advancements in military defense technology and the medical care field, visual identification and processing of data is critical to support the activities of the various personnel responsible for performing visually intensive analytical tasks. For example, in the case of military operations, improvements in the ability to efficiently identify and diagnose an injury in the field would reduce the mortality rate of injured military personnel. In addition, because the number of medically trained personnel is greatly constrained, there are limited resources that can be allocated to the screening, identification and treatment disease in the military or civilian fields. Thus, the ability to empower non-medical personnel to screen, identify and treat injuries occurring in both military and civilian fields by non-medical personnel through networked communication is highly desirable.

Furthermore, in addition to medical care, military personnel are required to fulfill a broad array of duties that requires specialized equipment. Due to the nature of such duties multiple pieces of equipment are typically required to be carried and managed by each individual. Because of the weight, and the complexity of the equipment, which can require several individual modules to be coupled together with a variety of communication cables, such equipment is significant in weight and adds to the burden placed on military personnel who are already under substantial physical stress in the field at times of combat.

Therefore, there is a need for a multi-purpose imaging and display system that provides a display, such as a wearable display, and a detector that is convertible between two or more operating modes, to reduce the total amount of equipment needed by military and medical personnel. Additionally, there is a need for a multi-purpose imaging and display system having convertible operating modes, whereby in a military combat-based mode, the multi-purpose imaging and display system is configured to perform predetermined functions, such as night-vision, remote sensing, and weapon aiming are enabled; and whereby in a medical care mode, the system is configured to perform predetermined functions, such as combat casualty care, image guided surgery for first responders, telemedicine and the like are enabled. In addition, there is a need for a multi-purpose imaging and display system that is capable of monitoring, sustaining and managing injured patients when medical assistance is unavailable, through the use of computer-based analysis or telemedical guidance. In addition, there is a need for a multi-purpose imaging and display system that is configured to enable network communication between multiple users to enable untrained individuals to provide medical care through remote collaboration with trained individuals.

SUMMARY OF THE INVENTION

In a first embodiment, the present invention provides a multi-purpose imaging and display system comprising: a display; a detector coupled to said display, said detector having a field of view; a filter in operative communication with said detector, such that said field of view is imaged by said detector through said filter, said filter configured to be sensitive to a first frequency spectrum; wherein said detector displays only objects within the field of view on said detector that emit one or more frequencies within the first frequency spectrum.

In a second embodiment, the present invention provides a multi-purpose imaging display system as in the first embodiment, further comprising a computing device coupled to said display and said detector;

In a third embodiment, the present invention provides a multi-purpose imaging display system as in either the first or second embodiment, wherein said display comprises a stereoscopic display adapted to be worn and viewed by a user.

In a fourth embodiment, the present invention provides a multi-purpose imaging display system as in any of the preceding embodiments, wherein said display is carried by a goggle system adapted to be worn by the user.

In a fifth embodiment, the present invention provides a multi-purpose imaging display system as in any of the preceding embodiments, wherein said display comprises a display selected from the group consisting of: a head-mounted display, an optical-see through display, a head-mounted projection display, a video see-through display, a selective occlusion see-through head-mounted display, a retinal scanning display, a switchable optical see-through display, and a video see-through display.

In a sixth embodiment, the present invention provides a multi-purpose imaging display system as in any of the preceding embodiments, wherein said detector comprises a detector selected from the group consisting of: an image intensifier tube, a micro-channel plate image intensifier, a thin-film image intensifier, a camera, and a 3D camera.

In a seventh fourth embodiment, the present invention provides a multi-purpose imaging display system as in any of the preceding embodiments, wherein said detector comprises a sensor selected from the group consisting of: a photodetector sensor, a charge-coupled device (CCD) sensor, a complementary metal-oxide semiconductor device sensor, a photomultiplier tube (PMT) sensor; an avalanche photodiode (APD) sensor, a thermographic sensor, and photodiodes.

In a eighth embodiment, the present invention provides a multi-purpose imaging display system as in any of the preceding embodiments, further comprising a communication interface coupled to enable communication with at least one other multi-purpose imaging and display system.

In a ninth embodiment, the present invention provides a multi-purpose imaging display system as in any of the preceding embodiments, wherein said communication interface enables cloud computing.

In a tenth embodiment, the present invention provides a multi-purpose imaging display system as in any of the preceding embodiments, further comprising a communication interface coupled to enable communication with at least one other computers, tablet computers or cell phones.

In an eleventh embodiment, the present invention provides a multi-purpose imaging display system as in any of the preceding embodiments, wherein said communication interface enables cloud computing.

In a twelfth embodiment, the present invention provides a multi-purpose imaging display system as in any of the preceding embodiments, further comprising a communication interface enabling cloud computing.

In a thirteenth embodiment, the present invention provides a multi-purpose imaging display system as in any of the preceding embodiments, further comprising a peripheral interface adapted to communicate with one or more peripherals.

In a fourteenth embodiment, the present invention provides a multi-purpose imaging display system as in any of the preceding embodiments, wherein said peripheral is selected from the group consisting optical spectrometer, absorption spectrometer, fluorescence spectrometer, Raman spectrometer, Coherent anti-Stokes Raman spectrometer, surface-enhanced Raman spectrometer, Fourier transform spectrometer, Fourier transform infrared spectrometer (FTIR), diffuse reflectance spectrometer, multiplex or frequency-modulated spectrometer, X-ray spectrometer, attenuated total reflectance spectrometer, electron paramagnetic spectrometer, electron spectrometer, gamma-ray spectrometer, acoustic resonance spectrometer, auger spectrometer, cavity ring down auger spectrometer, circular dichroism auger spectrometer, cold vapour atomic fluorescence auger spectrometer, correlation spectrometer, deep-level transient spectrometer, dual polarization interferometry, EPR spectrometer, force spectrometer, Hadron spectrometer, Baryon spectrometer, meson spectrometer, Inelastic electron tunneling spectrometer (LETS), laser-induced breakdown spectrometer (LIBS), mass spectrometer, Mössbauer spectrometer, neutron spin echo spectrometer, photoacoustic spectrometer, photoemission spectrometer, photothermal spectrometer, pump-probe spectrometer, Raman optical activity spectrometer, saturated spectrometer, scanning tunneling spectrometer, spectrophotometry, time-resolved spectrometer, time-stretch Spectrometer, thermal infrared spectrometer, ultraviolet photoelectron spectrometer (UPS), video spectrometer, vibrational circular dichroism spectrometer, X-ray photoelectron spectrometer (XPS).

In a fifteenth embodiment, the present invention provides a multi-purpose imaging display system as in any of the preceding embodiments, wherein said peripheral is selected from the group consisting of fiber microscope, handheld microscope, color microscope, reflectance microscope, fluorescence microscope, oxygen-saturation microscope, polarization microscope, infrared microscope, interference microscope, phase contrast microscope, differential interference contrast microscope, hyperspectral microscope, total internal reflection fluorescence microscope, confocal microscope, non-linear microscope, 2-photon microscope, second-harmonic generation microscope, super-resolution microscope, photoacoustic microscope, structured light microscope, 4Pi microscope, stimulated emission depletion microscope, stochastic optical reconstruction microscope, ultrasound microscope, and/or a combination of the aforementioned, and the like.

In a sixteenth embodiment, the present invention provides a multi-purpose imaging display system as in any of the preceding embodiments, wherein said peripheral is selected from the group consisting of ultrasound imager, reflectance imager, Diffuse reflectance Imager, fluorescence imager, Cerenkov imager, polarization imager, radiometric imager, oxygen saturation imager, optical coherence tomography imager, infrared imager, thermal imager, photoacoustic imager, spectroscopic imager, Raman Spectroscopic imager, hyper-spectral imager, fluoroscope, gamma imager, X-ray computed tomography, endoscope, laparoscope, bronchoscope, angioscope, and an imaging catheter.

In a seventeenth embodiment, the present invention provides a multi-purpose imaging display system as in any of the preceding embodiments, wherein said peripheral is one or more Raman spectrometers.

In an eighteenth embodiment, the present invention provides a multi-purpose imaging display system as in any of the preceding embodiments, wherein said peripheral is one or more ultrasound imaging systems.

In a nineteenth embodiment, the present invention provides a multi-purpose imaging display system as in any of the preceding embodiments, wherein said peripheral is one or more absorption spectrometers.

In a twentieth embodiment, the present invention provides a multi-purpose imaging display system as in any of the preceding embodiments, wherein said peripheral is one or more of fluorescence spectrometers.

In a twenty-first embodiment, the present invention provides a multi-purpose imaging display system as in any of the preceding embodiments, wherein said peripheral is one or more of vital sign sensors, said vital sign sensors monitoring one or more of: temperature, blood pressure, pulse, respiratory rate, ECG, EEG, pulse oximetry, and blood glucose.

In a twenty-second embodiment, the present invention provides a multi-purpose imaging display system as in any of the preceding embodiments, wherein said peripheral is selected from reflectance spectrometers, diffuse reflectance spectrometers, and diffuse reflectance imagers.

In a twenty-third embodiment, the present invention provides a multi-purpose imaging display system as in any of the preceding embodiments, wherein said peripheral is selected from in vivo microscopes and ex vivo microscopes.

In a twenty-fourth embodiment, the present invention provides a multi-purpose imaging display system as in any of the preceding embodiments, wherein said peripheral is one or more hyperspectral imaging systems.

In a twenty-fifth embodiment, the present invention provides a multi-purpose imaging display system as in any of the preceding embodiments, wherein said peripheral is one or more tracking module.

In a twenty-sixth embodiment, the present invention provides a multi-purpose imaging display system as in any of the preceding embodiments, wherein said tracking module is selected from the group consisting of optical tracking system, electromagnetic tracking system, radio frequency tracking system, gyroscope tracking system, video tracking system, acoustic tracking system, and mechanical tracking system.

In a twenty-seventh embodiment, the present invention provides a multi-purpose imaging display system as in any of the preceding embodiments, wherein said tracking module comprise LEDs and spectral filters.

In a twenty-eighth embodiment, the present invention provides a multi-purpose imaging display system as in any of the preceding embodiments, wherein said tracking module comprises software that enable topology sampling using a tracked handheld imaging probe or a tracked handheld sampling probe.

In a twenty-ninth embodiment, the present invention provides a multi-purpose imaging display system as in any of the preceding embodiments, wherein said peripheral is one or more global positioning system.

In a thirtieth embodiment, the present invention provides a multi-purpose imaging display system as in any of the preceding embodiments, wherein said peripheral is one or more robots.

In a thirty-first embodiment, the present invention provides a multi-purpose imaging display system as in any of the preceding embodiments, wherein said peripheral is one or more droid.

In a thirty-second embodiment, the present invention provides a multi-purpose imaging display system as in any of the preceding embodiments, further comprising a light source.

In a thirty-third embodiment, the present invention provides a multi-purpose imaging display system as in any of the preceding embodiments, wherein said light source includes a spectral filter.

In a thirty-fourth embodiment, the present invention provides a multi-purpose imaging display system as in any of the preceding embodiments, wherein said light source includes a white light-emitting diode.

In a thirty-fifth embodiment, the present invention provides a multi-purpose imaging display system as in any of the preceding embodiments, wherein said light source includes a surgical light having a plurality of individual light sources spaced apart to project light onto an object such that a shadow cast by an intervening object and one or more of said plurality of individual light sources is negated by at least one other of said plurality of individual light sources.

In a thirty-sixth embodiment, the present invention provides a multi-purpose imaging display system as in any of the preceding embodiments, wherein said light source is selected from white light-emitting diodes and polarizers.

In a thirty-seventh embodiment, the present invention provides a multi-purpose imaging display system as in any of the preceding embodiments, wherein said light source includes a white light source and a spectral filter filtering out a particular wavelength of light to avoid interference with an fluorescence emission wavelength.

In a thirty-eighth embodiment, the present invention provides a multi-purpose imaging display system as in any of the preceding embodiments, wherein said light source includes a laser diode and a diffuser.

In a thirty-ninth embodiment, the present invention provides a multi-purpose imaging display system as in any of the preceding embodiments, wherein said light source includes a projector and spectral filter.

In a fortieth embodiment, the present invention provides a multi-purpose imaging display system as in any of the preceding embodiments, wherein said light source includes a pulsed illumination device, or may utilize frequency modulation or pulse-duration modulation.

In a forty-first embodiment, the present invention provides a multi-purpose imaging display system as in any of the preceding embodiments, wherein said detector may detect signals of a given frequency or spectrum, and the light source may correlate the detected signal with the frequency modulation and pulse-duration modulation.

In a forty-second embodiment, the present invention provides a multi-purpose imaging display system as in any of the preceding embodiments, wherein said light source comprise illumination that offer adjustable components that overlap with emission spectra.

In a forty-third embodiment, the present invention provides a multi-purpose imaging display system as in any of the preceding embodiments, wherein said computing device comprises memory modules that stores educational contents.

In a forty-fourth embodiment, the present invention provides a multi-purpose imaging display system as in any of the preceding embodiments, wherein said memory modules that stores educational contents comprises memory modules that stores medical training contents.

In a forty-fifth embodiment, the present invention provides a multi-purpose imaging display system as in any of the preceding embodiments, wherein said memory modules that stores educational contents comprises memory modules that stores military training contents.

In a forty-sixth embodiment, the present invention provides a multi-purpose imaging display system as in any of the preceding embodiments, where said filter selectively movable out of communication with said detector In a forty-seventh embodiment, the present invention provides a method for visualizing educational contents, said method comprising: obtaining educational contents from remote computers using a multi-purpose imaging and display system in accordance with any of the preceding embodiments; observing the educational contents using a multi-purpose imaging and display system in accordance with any of the preceding embodiments.

In a forty-eighth embodiment, the present invention provides a method for capturing sending, receiving and visualizing educational contents, said method comprising: capture images as educational contents using a multi-purpose imaging and display system in accordance of with any of the preceding embodiments; sending images from a multi-purpose imaging and display system in accordance of with any of the preceding embodiments to another a multi-purpose imaging and display system in accordance with any of the preceding embodiments; observing the images as educational contents using a multi-purpose imaging and display system in accordance with any of the preceding embodiments.

In a forty-ninth embodiment, the present invention provides a method in accordance with the above embodiment, further comprising: record audio as educational contents using a multi-purpose imaging and display system in accordance with any of the preceding embodiments; sending audio recorded from a multi-purpose imaging and display system in accordance of with any of the preceding embodiments to another multi-purpose imaging and display system in accordance of with any of the preceding embodiments; listen to the audio as educational contents using a multi-purpose imaging and display system in accordance of with any of the preceding embodiments.

In a fiftieth embodiment, the present invention provides a method in accordance with the above embodiment, a method for imaging forensic evidence, said method comprising: applying fluorescent forensic tracers to the environment and observing the environment using a multi-purpose imaging and display system.

In a fifty-first embodiment, the present invention provides a multi-purpose imaging and display system comprising: a goggle having a display for viewing by the eyes of one wearing the goggle; a detector coupled to said display, said detector having a field of view and projecting an image of that field of view onto said display; a peripheral interface for selectively communicating with a peripheral device, said peripheral device providing an additional functionality.

In a fifty-second embodiment, the present invention provides a multi-purpose imaging and display system as in the fifty-first embodiment, wherein the peripheral may be selected from any of the multitude of peripherals disclosed in any of the embodiments above.

In a fifty-third embodiment, the present invention provides a multi-purpose imaging and display system as in the fifty-first or fifty-second embodiment, wherein the additional functionality is selected from additional imaging, sensing data, and tracking data, said tracking data relating to one or more of the location of an object in the field of view, the location of the goggle and the location of peripherals.

In a fifty-fourth embodiment, the present invention provides a multi-purpose imaging and display system comprising: a plurality of goggles, each including: a display for viewing by the eyes of one wearing the goggle, a detector coupled to said display, said detector having a field of view and projecting an image within that field of view onto said display, and a communication interface linking each of said plurality of goggles to communicate with each other.

BRIEF DESCRIPTION OF THE DRAWINGS

These and other features and advantages of the present invention will become better understood with regard to the following description, appended claims, and accompanying drawings wherein:

DETAILED DESCRIPTION OF THE INVENTION

Figure 1:
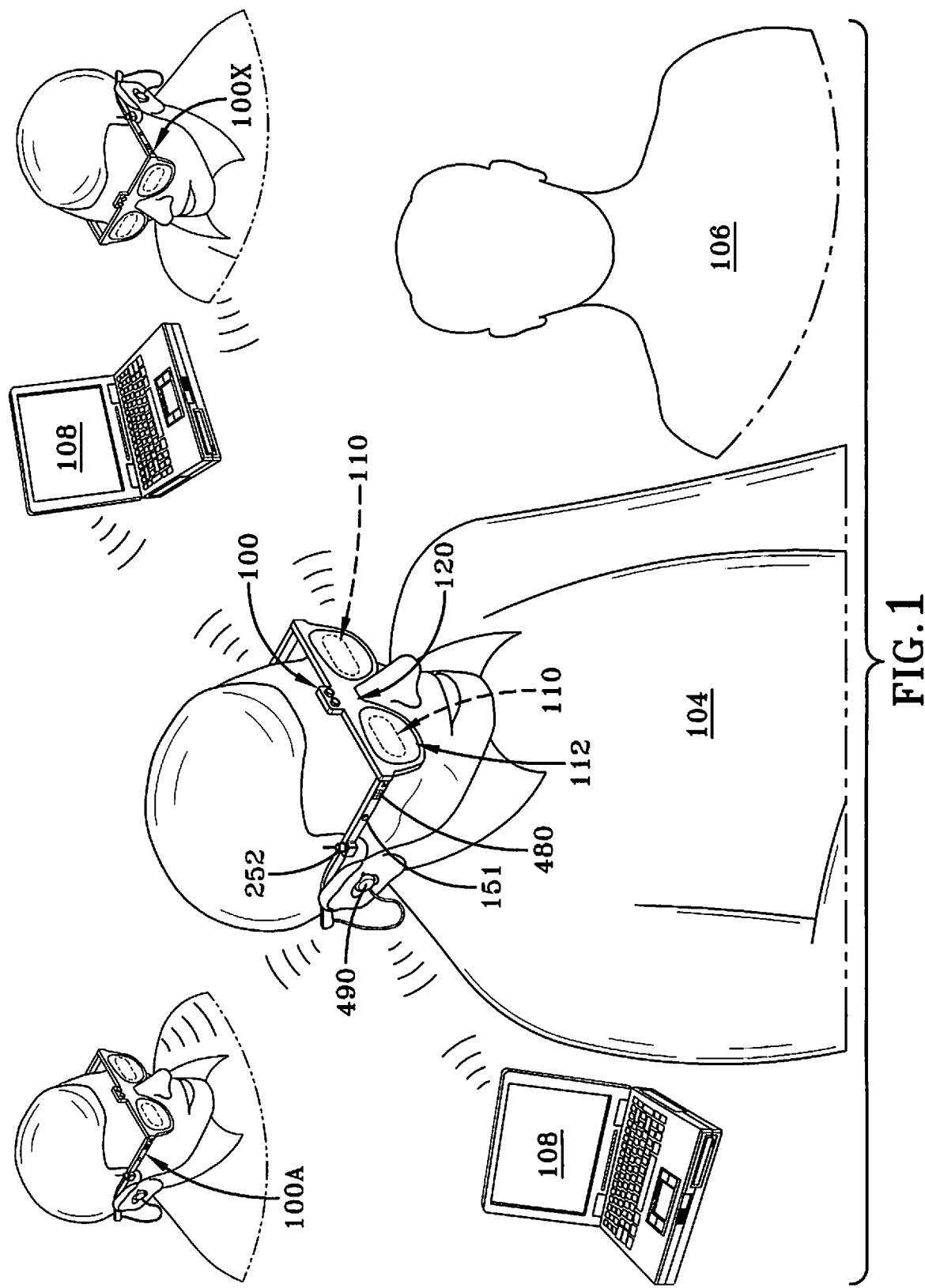
FIG. 1 is a perspective view of a multipurpose imaging and display system in accordance with the concepts of the present invention.
Figure 2:
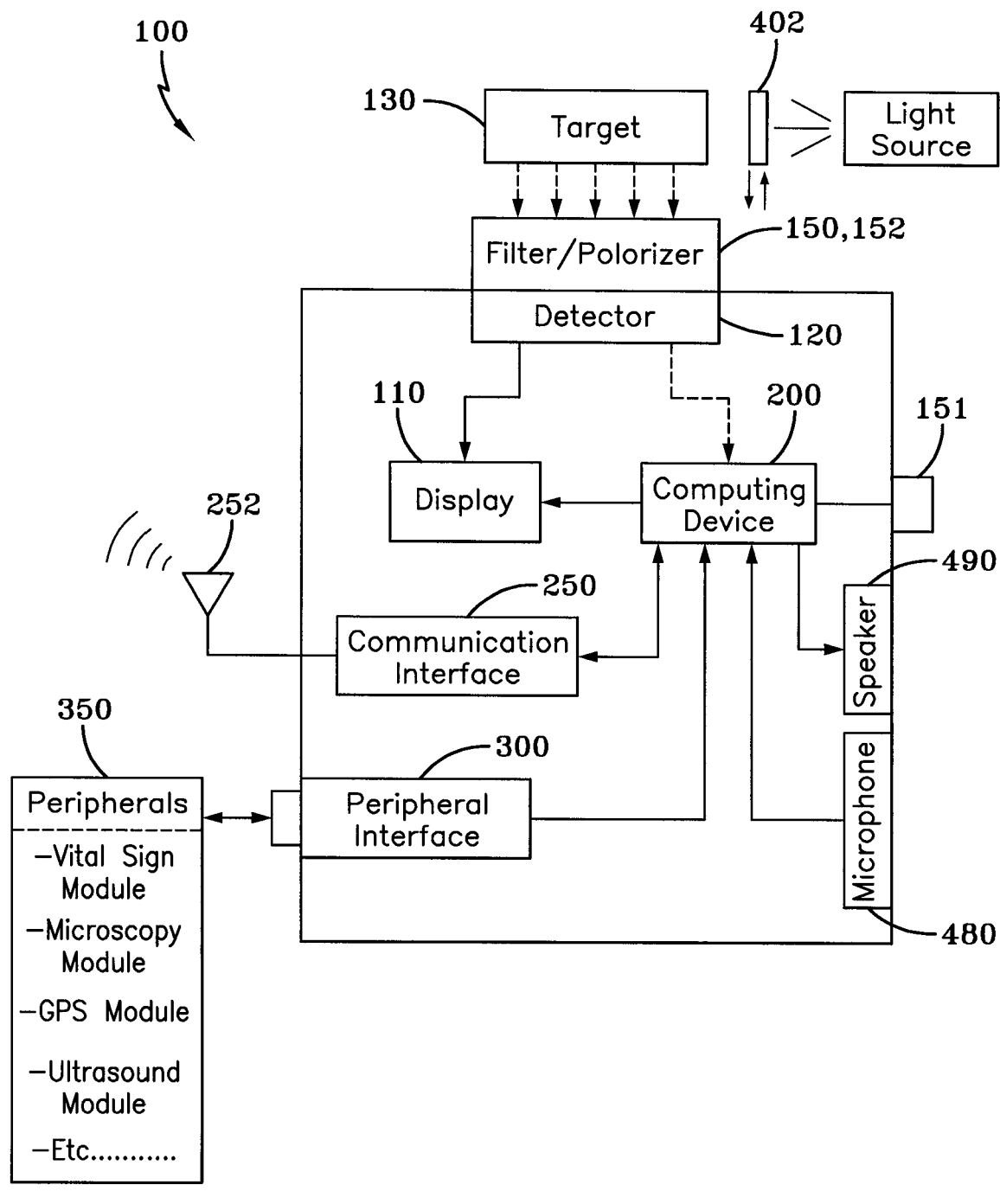
FIG. 2 is a schematic diagram showing the components of the multipurpose imaging and display system in accordance with the concepts of the present invention.

A multi-purpose imaging and display system is generally referred to by reference numeral 100, as shown in FIG. 1 of the drawings. The system 100, shown in detail in FIG. 2, includes a display 110, which may comprise any suitable display, and, in some embodiments, is a wearable display that is configured for being attached to and worn by a user 112. For example, such a wearable display 110 may be included as part of a goggle-type wearable device 114 shown in FIG. 1, which comprises a wearable goggle or eye-piece frame that carries the display 110.

In one aspect, the display 110 may comprise a single display element suitable for providing a single, continuous display that provides a single display surface that encompasses the totality of the user's field of view, or portion thereof. Alternatively, multiple separate display elements, may be used by the display, such as a dedicated right and a dedicated left display, such as in the case of a stereoscopic display, which provides an independent displays, designated as 110A and 110B (FIG. 1), to provide the field of view of each user's eye.

Furthermore, the display 110 may comprise an LCD (liquid crystal display) display, an OLED (organic light emitting diode) display, a projection display; a head-mounted display (HMD), a head-mounted projection display (HMPD), an optical-see through display, a switchable optical see-through display, a selective occlusion see-through head-mounted display, and a video see-through display. Furthermore, the display 110 may comprise an augmented reality window, augmented monitors, a projection on the patient/projective head-mounted display, selective occlusion see-through head-mounted display, and retinal scanning display. In another aspect, the display 110 may be configured to display any static or moving image. The display 110 may also comprise a picture-in-picture (PIP) display that can display images from multiple independent image sources simultaneously. In one aspect, the display 110 may comprise a 3D display capable of displaying 3-dimensional images. In still another embodiment, the display 110 may be configured to provide overlaid images of various opacity/transparency to allow simultaneous viewing of multiple images on the display 110 at one time. In yet another embodiment, the display 110 may be at least partially transparent to allow a user to view the image being displayed, while allowing the user to simultaneously see through the display 110 to also view the user's surrounding environment at the same time.

Coupled to the display is a detector 120, which is configured to capture any desired static or moving image data from a target of interest (TOI) 130, which may comprise any desired object, such as a wound shown in FIG. 1. That is, the detector 120 includes a field of view that captures image data of the target of interest 103 that is within the field of view. It should also be appreciated that the detector 120 may be used in conjunction with any suitable optical lens or optical assembly to provide any desired field of view, working distance, resolution and zoom level. In one aspect, the detector 120 may comprise a camera, such as a charge-coupled device (CCD), a complementary metal-oxide semi-conductor device (CMOS), one or more photomultiplier tubes (PMT), one or more avalanche photodiodes (APD), photodiodes, and a thermographic camera, such as an infra-red detector. In addition, the detector 120 may comprise one or more image intensifier tubes, a micro-channel plate image intensifier, and a thin-film image intensifier.

In some embodiments, the detector is a single detector 120. In one embodiment, the detector 120 may comprise a stereoscopic detector, which includes multiple imaging sensors or cameras designated respectively as 120A and 120B, as shown in FIG. 1, which take stereoscopic images that can be displayed at stereoscopic display 110 with depth perception.

Figure 3A:
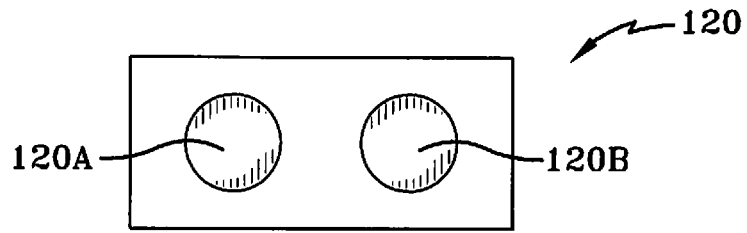
FIG. 3A is schematic diagram showing the components of a detector provided by the multipurpose imaging and display system when configured with stereoscopic imaging sensors in accordance with the concepts of the present invention.

In another embodiment, the detector 120 may comprise a stereoscopic detector, which includes multiple imaging sensors or cameras designated respectively as 120A and 120B, as shown in FIGS. 1 and 3A, whereby each individual camera 120A-B includes multiple individual sensor elements. For example, the cameras 120A-B may be each configured with a first and second sensor element, whereby the first sensor element provides for full-color imaging and the second sensor element provides selective or switchable florescence imaging. Further discussion of various configurations of the various sensor elements that form the cameras 120-B will be discussed in detail below.

The detector 120 may be configured to perform one or more imaging modes, including but not limited to fluorescence imaging, thermal imaging, oxygen saturation imaging, hyperspectral imaging, photo acoustic imaging, interference imaging, optical coherence tomography imaging diffusing optical tomography imaging, ultrasound imaging, nuclear imaging (PET, SPECT, CT, gamma, X-ray), Cerenkov imaging, and the like. In addition, the detector 120 may also be configured to perform real-time/offline imaging, including absorption, scattering, oxygenation saturation imaging, fluorescence imaging, fluorescence lifetime imaging, hyperspectral imaging, polarization imaging, IR thermal imaging, bioluminescence imaging, phosphorescence imaging, chemiluminescence imaging, scintillation imaging, and the like.

In some embodiments, the display 110 and the detector 120 are coupled to a computing unit 200. The computing unit 200 may be part of a wearable version of the system 100 or might alternatively be an external computing unit 200. The computing unit 200 includes the necessary hardware, software or combination of both to carry out the various functions to be discussed. In one aspect, the computing unit 200 may comprise a microprocessor or may comprise any other portable or standalone computing device, such as a smartphone, capable of communicating with the various components of the system 100. It should also be appreciated that the computing system 200 may also include a memory unit to store various data to be discussed. In addition, the computing unit 200 is configured, whereby the image data acquired by the detector 120 may be processed and transmitted by the computing unit 200 in various manners to be discussed. It should also be appreciated that the computing unit 200 may include a local or remotely accessible memory unit, which allows the computing unit to store and/or acquire various programs, algorithms, databases, and decision support systems that enable a variety of functions to be discussed, which may be based on the image data collected by the detector 120. In one aspect the system 100 may be powered by any suitable power source, such as a portable power source comprising one or more batteries or a plug-in type power source for connection to a standard electrical wall outlet.

In operative communication with the field of view of the detector 120 is a filter 150. Accordingly, the filter 150 serves to process the light that travels from the target of interest (TOI) 130 before the light is received at the detector 120 in the form of image data. As such, the filter 150 is configured to use any suitable technique to process the image data collected by the field of view of the detector 120. In one aspect, the system 100 may be configured so that filter 150 is brought into or out of operative communication with the detector 120, so that the image data collected by the field of view of the detector 120 is selectively filtered or unfiltered. In one aspect, the selective filtering performed by the filter 150 may be carried out by any suitable mechanism, such as an electro-mechanical mechanism, which is initiated by any suitable switching device 151, such as a mechanical switch, or voice command to move the filter 150. Accordingly, when the switchable filter 150 is in operative communication with the detector 120, the system 100 is placed into a first mode for detecting TOIs 130 that emit frequencies within a spectrum of frequencies defined by the physical parameters of the filter, such as the spectrum of frequencies emitted during the fluorescence of materials. Alternatively, when the filter 150 is not in operative communication with the detector 120, the system 100 is placed into a second mode for detecting TOIs 130 within another frequency spectrum, such as a night vision frequency spectrum.

It should be appreciated that the filter 150 may comprise a filter wheel having different discrete filters of different filtering properties, which can be selectively rotated into operative alignment with the detector 120. In addition, the filter 150 may comprise a long-pass filter, a band-pass filter, a tunable filter, a switchable filter, and the like. In another aspect, the filter 150 may comprise an 830 nm band-pass filter.

In other embodiments, the filter 150 may be replaced by a polarizer 152 and operate in the same manner with respect to the detector 120 as discussed above with regard to the filter 150. Furthermore, in other embodiments the polarizer 152 may be simultaneously used together with the filter 150, whereby the field of view of the detector 120 is processed by both the polarizer 152 and by the filter 150 prior to detection by the detector 120. It should also be appreciated that the polarizer 152 may comprise a switchable polarizer that operates in the same manner as the switchable filter 150, or may comprise a tunable polarizer.

Accordingly, the ability to selectively filter or selectively polarize the field of view being detected by the detector 110 embodies a "convertible" system, whereby when the detector 110 is unfiltered, it is in a first mode, which is capable of a first imaging state, such as night vision for military use; and when the detector is placed or "converted" into its second mode, it is capable of a second imaging state, whereby it is capable of fluorescence imaging in medical applications for example.

Furthermore, using the combination of the cameras 120A-B each having multiple imaging elements together with the selective use of the filter 150 or polarizer 152 allows for a variety of modes of operation. For example, in FIGS.

Figure 3B:
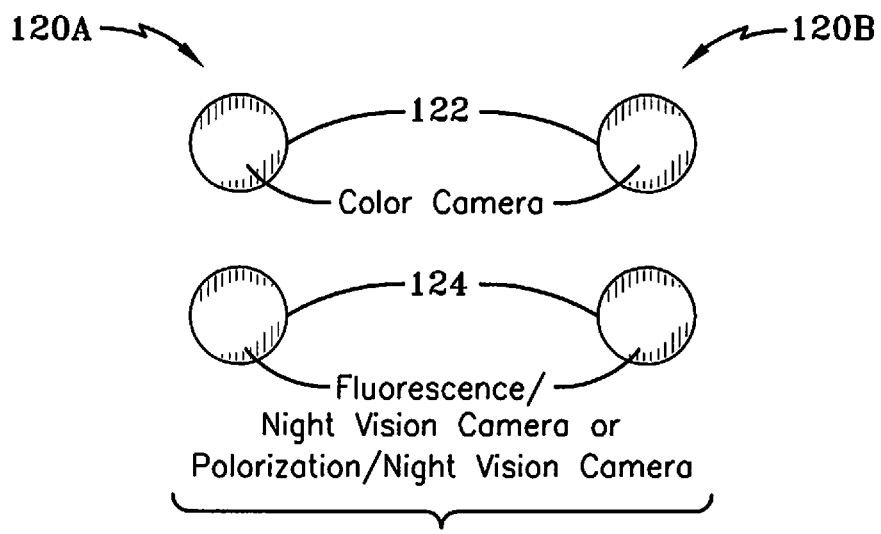
FIG. 3B is a schematic diagram of an alternative configuration of the detector, whereby multiple sensor element types are used for each of the stereoscopic imaging sensors shown in FIG. 3A in accordance with the concepts of the present invention.
Figure 3C:
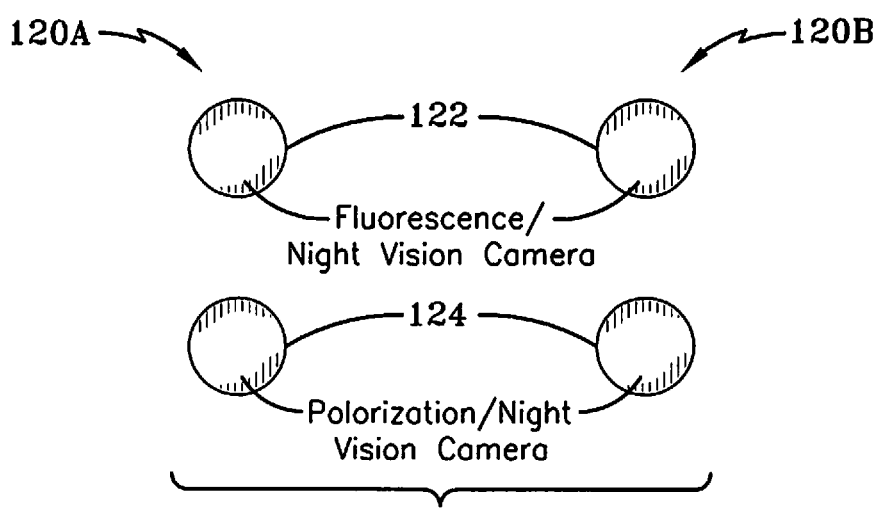
FIG. 3C is a schematic diagram of another configuration of the detector, whereby multiple sensor element types are used for each of the stereoscopic imaging sensors shown in FIG. 3A in accordance with the concepts of the present invention.
Figure 3D:
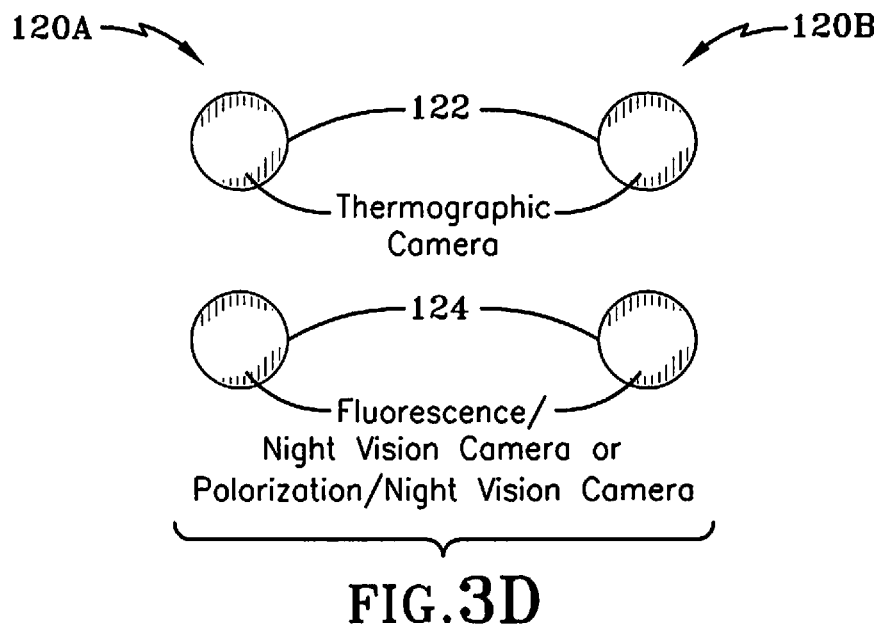
FIG. 3D is a schematic diagram of a further configuration of the detector, whereby multiple sensor element types are used for each of the stereoscopic imaging sensors shown in FIG. 3A in accordance with the concepts of the present invention.
Figure 3E:
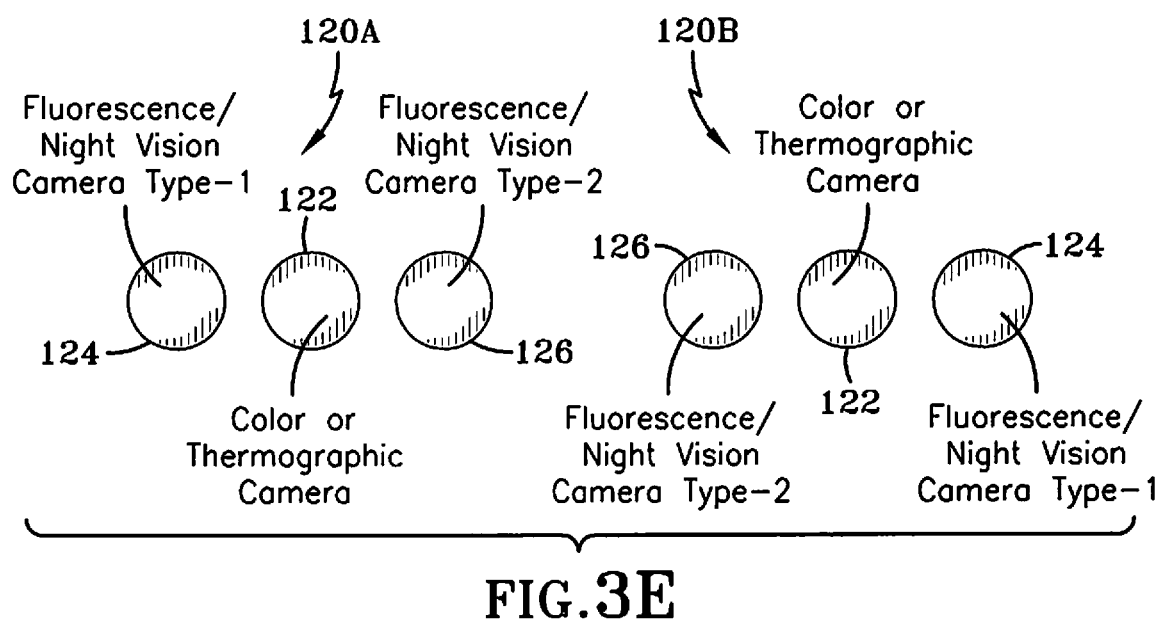
FIG. 3E is a schematic diagram of another configuration of the detector, whereby multiple sensor element types are used for each of the stereoscopic imaging sensors used for each of the stereoscopic imaging sensors shown in FIG. 3A in accordance with the concepts of the present invention.

3B-D the detector 120 is configured such that each camera 120A and 120B has two sensor elements 122 and 124, whereby the first sensor element 122 is used for a first imaging mode (or a convertible detection mode that is switchable between among two or more imaging modes) and the second sensor element 124 is used for a second convertible imaging mode, which provides selective imaging among two or more imaging modes. Thus, in FIG. 3B, sensor element 122 of cameras 120A-B are operate in a color imaging mode, while sensor elements 124 of cameras 120A-B operate in a convertible filter mode, that can be switched between florescence imaging with different spectral frequencies; or between polarization imaging with different polarization states. In addition, FIG. 3C shows that the sensor element 122 of cameras 120A-B is switchable between different modes of fluorescence imaging, while sensor element 124 of cameras 120A-B are switchable between different modes of polarization imaging. Furthermore, FIG. 3D shows that the sensor element 122 of cameras 120A-B is a thermographic sensor, while sensor element 124 of cameras 120A-B are switchable between different modes of fluorescence imaging; or switchable between different modes of polarization imaging. Additionally, FIG. 3E shows the use of three sensor elements, whereby sensor element 124 of cameras 120A-B offer a first-type of fluorescence imaging modes; sensor element 122 of cameras 120A-B is offer color imaging or thermographic imaging; and the sensor element 126 of cameras 120A-B offers a second-type of fluorescence imaging modes.

Coupled to the computing system 200 is a communication interface 250, which includes a suitable antenna 252 for communicating wirelessly or via a wired connection with a communication network 260. The system 100 may communicate via the communication network 260 with other multipurpose imaging and display devices 100A-X, or any other networked computer system 262, such as laptop computers, smart phones, and the like, as shown in FIG. 1. In one aspect, the communication interface 250 is embodied as a transceiver that is enabled to both transmit and receive data via the network 260. In one aspect, the communication interface 250 may be configured to communicate over the network 260 using any suitable method, including RF (radio frequency) signals, such as a low-power RF signals, a wired or wireless Ethernet communication, WiFi communication, Bluetooth communication, and the like. As such, the ability of multiple systems 100 to communicate with each other enables a variety of functions, which will be discussed in detail below. The communication will allow one or more of sharing of detector images and images provided by peripherals (described below) and sound and software educational modules (described below).

The communication interface 250 also enables network and cloud computing features to be carried out by the imaging and display system 100. In one aspect, the communication interface 250 allows the system 100 to communicate with a remote storage devices on a remote network or a remote cloud computing system, generally represented by the numeral 270, as shown in FIG. 1 to allow access centralized data storage, conduct further computing analysis, access to other software applications, and to enable record storage.

Also coupled to the computing device 200 is a peripheral interface 300. The peripheral interface may comprise a wired or wireless interface that allows for the addition of one or more peripherals 350 to be selectively added to the imaging and detection system 100. The peripherals may comprise one or more sensors and detectors. For example, such add-on peripheral 350 may include a vital sign sensor module, that may monitor one or more of: temperature, blood pressure, pulse, respiratory rate, ECG, EEG, pulse oximetry, blood glucose, and the like. The peripheral 350 may also include an ultrasound module, a spectroscopy module (e.g. Raman spectroscopy, absorption spectroscopy, and reflectance spectroscopy), a GPS (global positioning system) module, a microscope module (e.g. a handheld microscope, a fiber-based in-vivo microscope, and a traditional microscope), and a non-microscopic imaging module (hyperspectral imaging, photoacoustic imaging, optical coherence imaging).

In another aspect, the peripheral 350 may comprise a probe instrument, such as a hand-held probe. As such, the hand-held probe may be used for any desired type of microscopy. In some embodiments the probe is employed for in vivo microscopy. The probe may utilize various detection methods, such as color microscopy, reflectance microscopy, fluorescence microscopy, oxygen-saturation microscopy, polarization microscopy, infrared microscopy, interference microscopy, phase contrast microscopy, differential interference contrast microscopy, hyperspectral microscopy, total internal reflection fluorescence microscopy, confocal microscopy, non-linear microscopy, 2-photon microscopy, second-harmonic generation microscopy, super-resolution microscopy, photoacoustic microscopy, structured light microscopy, 4Pi microscopy, stimulated emission depletion microscopy, stochastic optical reconstruction microscopy, ultrasound microscopy, and/or a combination of the aforementioned, and the like.

In another aspect, the handheld probe used as the peripheral 350 may be a higher resolution imaging device that has not reached microscopic resolution yet. In some embodiments, the non-microscopic imaging method is selected from one or more of the following: reflectance imaging, fluorescence imaging, Cerenkov imaging, polarization imaging, ultrasound imaging, radiometric imaging, oxygen saturation imaging, optical coherence tomography, infrared imaging, thermal imaging, photoacoustic imaging, spectroscopic imaging, hyper-spectral imaging, fluoroscopy, gamma imaging, and X-ray computed tomography. The physical form of the handheld probe may comprise an endoscope, a laparoscope, a bronchoscope, an angioscope, and a catheter for angiography.

In still another example, the handheld probe may be a non-imaging device or a sensing device, such as a fiber-based spectrophotometer. In addition, different spectroscopies may be realized from use of a suitable peripheral 350, such as various optical spectroscopies, absorption spectroscopy, fluorescence spectroscopy, Raman spectroscopy, Coherent anti-Stokes Raman spectroscopy (CARS), surface-enhanced Raman spectroscopy, Fourier transform spectroscopy, Fourier transform infrared spectroscopy (FTIR), multiplex or frequency-modulated spectroscopy, X-ray spectroscopy, attenuated total reflectance spectroscopy, electron paramagnetic spectroscopy, electron spectroscopy, gamma-ray spectroscopy, acoustic resonance spectroscopy, auger spectroscopy, cavity ring down spectroscopy, circular dichroism spectroscopy, cold vapour atomic fluorescence spectroscopy, correlation spectroscopy, deep-level transient spectroscopy, dual polarization interferometry, EPR spectroscopym, force spectroscopy, Hadron spectroscopy, Baryon spectroscopy, meson spectroscopy, Inelastic electron tunneling spectroscopy (IETS), laser-induced breakdown spectroscopy (LIES), mass spectroscopy, Mössbauer spectroscopy, neutron spin echo spectroscopy, photoacoustic spectroscopy, photoemission spectroscopy, photothermal spectroscopy, pump-probe spectroscopy, Raman optical activity spectroscopy, saturated spectroscopy, scanning tunneling spectroscopy, spectrophotometry, time-resolved spectroscopy, time-stretch Spectroscopy, thermal infrared spectroscopy, ultraviolet photoelectron spectroscopy (UPS), video spectroscopy, vibrational circular dichroism spectroscopy, X-ray photoelectron spectroscopy (XPS), or a combination of the aforementioned.

In other embodiments, the peripheral 350 is selected from robots, droids and global positioning systems.

Tracking and Registration of Multiple Images for Display

In some embodiments, the system 100 includes a tracking module, which can be considered another peripheral 350, and includes software suitable for tracking the spatial location of the detector 120 (or 120A, 120B) and the location of peripherals 350, such as imaging cameras and probes, and registering these locations relative to the image(s) of the detector 120 or detectors 120A, 120B (in stereoscopic modalities). Reference to detector 120 herein will also be understood to be equally applicable to the stereoscopic modalities of those systems 100 employing detectors 120A and 120B. Thus, the corresponding imaging and sensing information obtained from the peripheral 350 can be correlated with the field of view imaged by the detector 120 of the multipurpose imaging and display system 100. That is, the system 100 may be programmed to utilize image tracking and registration techniques to allow for the overlay of multiple images acquired directly by the detector 120 of the system 100 with those images acquired by peripheral image detectors, such as hand-held microscopy probes, or the like. In some embodiments, the tracking module can also track and register the location of other non-peripheral elements, such as the tools being employed by military or medical personnel. For example, the location of scalpels or clamps or stents or other elements of a medical operation could be tracked and registered with the images. It should be appreciated that the software enabling such tracking and registration features may be provided from a remote computer system to the system 100 via the network 260 or stored on any peripheral attached to the peripheral interface 300. Specifically, tracking techniques utilized by the system 100 obtain the position of a patient to be treated using the system 100, the system 100 itself comprising the wearable display 114, and the handheld imaging peripheral 350 coupled to the peripheral interface 300.

The tracking functions may be carried out using optical tracking or magnetic tracking devices that are employed as a peripheral 350. If optical tracking is used, active markers such as LEDs may be attached to detector 120, the imaging or sensing probe employed as another peripheral 350, and the patient or other desired object, to locate their locations, respectively. NDI Optotrak Certus system is an example of optical tracking systems that may be used for this embodiment. Commercially available optical tracking systems may consist of CCD cameras and sequentially illuminated infrared (IR) LEDs, and can be easily integrated as a peripheral 350 into the wearable imaging and display device 100. Alternatively, one may use a videometric system to estimate patient pose (or object positioning) and instrument orientation by identification of passive markers in video-image sequences.

In one aspect, optical tracking using NDI Optotrak Certus may be incorporated as a peripheral 350 to provide tracking, whereby light emitting diodes (LED) are attached to the wearable device 100 that carries the detector 120, and imaging module as another peripheral 350, such as ultrasound and hand-held microscopy probes and patients. As such, the LEDs attached to the detector 120, hand-held probe as a peripheral 350, and patients are tracked by the NDI Optotrak Certus system.

In another embodiment, a novel infrared optical tracking method may be utilized by the system 100. As such, the wavelength of the optical emitters for tracking purposes (such as LEDs) attached to the patient, wearable imaging and display system 100, and intraoperative imaging peripheral 350 may be different wavelengths from the wavelengths detected by the detector 120, and imaging peripheral 350. Methods, such as spectral filtering may be used to facilitate the separation of wavelengths between the optical emitter from the tracking system and the detection of the detector 120, and imaging peripheral 350. Frequency modulation may also be used to separate the signal from the tracking optical emitters from the signal of interest of the detector 120, and imaging peripheral 350.

In another example, gyroscopic tracking in combination with video tracking may be performed using the module 350.

If electromagnetic tracking is used, the peripheral 350 may incorporate small coils or similar electromagnetic field sensors and multiple position measurement devices. The electromagnetic field sensors may be attached to detector 120, the imaging or sensing probe employed as another peripheral 350 and the patients, to locate their locations, respectively.

Alternatively, the tracking functions may be carried out using fiducial markers, such as LEDs, attached to (a) the patient to be treated or an object to be acted upon or observed (in the instance of non-medical applications), (b) the wearable imaging and display device 100, and (c) the peripheral 350. Through the use of fiducial markers, images of the same subject produced with multiple distinct imaging systems—for example, the detector 120 as a first imaging system, and any desired peripheral 350 that generates a second image as the second imaging system—may be correlated by placing fiducial markers in the area imaged by both systems. Appropriate software correlates the two images, and in the case of the present invention, permits viewing of the two (or more) images overlaid together or in a picture-in-picture format.

With the position obtained using the tracking techniques described, enabled by tracking systems as a peripheral 350, registration, or alignment, of the different images obtained by the imaging and display system 100 and the handheld imaging probe employed as another peripheral 350 is performed by using transformation matrices between the object being imaged by the detector 120 (detector image space) and images and locations of the peripherals 350 (peripheral image space) can be calculated. Specifically, the image registration process is carried out such that the image captured by detector 120 and peripheral locations and images can be registered together as a single image. As a result, the co-registered images from the detector 120 of the wearable system 100 and the image peripheral 350 can be displayed in the wearable display in an overlaid and aligned manner.

It should also be appreciated that in addition to the tracking techniques described above, other tracking techniques may be used, such as radio frequency tracking, gyroscope tracking, video tracking (pattern recognition), acoustic tracking, mechanical tracking, and/or a combination thereof. In addition, the tracking method employed by the module 350 may utilize rigid body, flexible body or digitizer methods.

It should also be appreciated that in addition to the registration techniques discussed above, other registration techniques may be used, such as point-based registration, surface-based registration, and/or a combination thereof. The registration may comprise either intensity-based or feature-based registration. The transformation models used may comprise linear transformation, or non-rigid/elastic transformation. Spatial or frequency domain methods may be used, as well as automatic or interactive methods.

To sample the topology of the object/physical space in the field of view (or the target of interest), digitizers (such as the device from NDI) may be used to sample the points in physical space. Alternatively, topology acquisition systems, such as a 3D scanner may be used to capture the 3D topology, which may facilitate image registration.

In some embodiments, a handheld probe employed as a peripheral module 350 may serve dual purposes: serving as stylus/digitizer for sampling topology; and serving as imaging or sensing probe. Specifically, the handheld probe may have optical emitters such as LEDs attached to it, which will allow location of the tip of the handheld probe with the help of the optical tracking system. Alternatively, the position of the tip can be obtained by tracking the electromagnetic sensors attached to the handheld probe using a magnetic tracking system. When the probe are swiped across different points on the surface of the organs, a 3D point cloud can be established, based on the locations of the tips of handheld probe (tip is considered to be just in contact with organs). In this way, the imaging handheld probe also enables similar functionality to sample topology as the non-imaging stylus/digitizer traditionally employed in tracking systems.

In another aspect, a tracking system employed as a peripheral module 350 may track the positions of an imaging peripheral (e.g., a hand-held microscopy probe peripheral) also employed as a peripheral module 350, and register the image taken with the imaging peripheral with the image generated by the detector 120, and display it in the display 110. As such, the images detected by the imaging peripherals, such as a ultrasound probe may then be overlaid with images collected, such as fluorescence images, by the detector 120 of the imaging and display system 100 for presentation on the display 110. The registration of multiple images on the display 110 may be achieved using any suitable technology, including point-based registration, surface-based registration, intensity-based, feature-based registration, and/or a combination of both. The transformation models used may comprise linear transformation, or non-rigid/elastic transformation. Spatial or frequency domain methods may be used, as well as automatic or interactive methods. For example, fiducial markers, such as LEDs, may be used to facilitate point-based registration. In another example, if surface topology or profile is available, the surface-based registration can also be used. In yet another example, the registration may also be based on pattern recognition or feature-based recognition.

Thus, by combining the functionality of the communication interface 250 and the peripheral interface 300, the system 100 is enabled to provide multiple functions. One or more peripherals of a multitude of types, including those mentioned above can be selectively coupled to the display system 100, as needed for providing the system 100 with a desired functionality. If imaging from a probe is needed in a given application, for example for in vivo imaging of a patient, a probe as a peripheral 350 can be coupled to the display system 100 at the interface 250 so that the display system 100 would then have the ability to display the image gathered from the probe. As per the tracking disclosure above, this image could be overlaid onto the image of the patient gathered by the detector 120, placing the in vivo image of the probe employed as a peripheral 350 at the proper location on the image of the patient.

In another aspect, a co-registration of a 4 sensor setup between color and fluorescence imaging, whereby vertical and horizontal disparities are correlated. In particular, this example describes the manner in which a 4 camera setup is used to register intraoperative color imaging to intraoperative fluorescence imaging.

In another embodiment, stereoscopic fluorescence images captured by 2 fluorescence cameras and stereoscopic color images captured by 2 color cameras can be registered together. Both sets of images were placed into side-by-side frames, and the fluorescent side-by-side frame was overlaid onto the anatomical frame by the computing module and sent to the display. For high registration accuracy, we measure the vertical distance from the center of the filtered cameras for fluorescence to the center of the unfiltered color camera as well as the horizontal baseline distance between two filtered or unfiltered cameras. From this information, a correction metric, $D_V$, was determined from the equation:

$$\frac{L_H}{L_V} = \frac{D_H}{D_V}$$

where L is the measured baseline disparity between cameras in either the horizontal (H) or vertical (V) direction, and $D_H$ is the horizontal pixel disparity between common points in the left and right fluorescent images. The points used to calculate $D_H$ were the peak fluorescent points; if more than one peak existed, one was chosen for the calculation. The fluorescent frames were then shifted up by the calculated correction metric so that, after calibration, the fluorescent image was aligned to the corresponding color image.

In addition, GPS and wireless communication between multiple imaging and display systems 100A-X can be integrated, such that information relevant to military or medical environments is labeled with GPS data. Thus, in one embodiment, information acquired by each system 100A-X can also be transmitted or received wirelessly, to guide battle or medical interventions. Using telemedicine functionality of the system 100, medical operations can be performed by first responders using the system 100 under the guidance of medical practitioners that are located remotely but who are also using the system 100. It should be appreciated that the systems 100A-X may also communicate with any other suitable computing device, such as a tablet, mobile smart phone, or the like.

In addition, the system 100 may include an illumination or light source 400 to illuminate the field of view used to image the target object of interest 130 being imaged by the detector 120. It should also be appreciated that the light source 400 is configured to deliver a light having the appropriate intensity and frequency spectrum that is compatible with the particular imaging being conducted with the detector 120, with or without the filter/polarizer 150,152. For example, it may be necessary to have a light source 400 that emits a first frequency spectrum for use in a first imaging mode, such as a night vision imaging mode, and that emits a second frequency spectrum for use in a second imaging mode, such as a fluorescence imaging mode. In one aspect, the light source 400 may be coupled to the computing device 200 for automated control over the functions provided by the light source 400, or may be unattached from the computing device 200 and operated manually by the user of the system 100.

It should also be appreciated that the light source 400 may serve different purposes in both the military environment and the medical environment. For example, the light source 400 may be used in military applications for enabling weapon aiming, for guiding laser guided weaponry, or for night vision. Furthermore, upon conversion of the detector 120 by removal or the filter/polarizer 150,152 or by selecting the necessary filter/polarizer 150,152 the illumination of the light source 400 may be used for florescence imaging, optical imaging, photodynamic therapy, laser surgery, sterilization, and the like. It should also be appreciated that multiple light sources 400 may be used.

It should also be appreciated that the light source 400 may comprise a laser light; a light emitting diode (LED), such as a white LED; an incandescent light; a projector lamp; an arc-lamp, such as xenon, xenon mercury, or metal halide lamp; as well as coherent or in-coherent light sources.

The light source 400 may also comprise a digital (LED-based) projector lamp, and additionally the light source may project spatial frequencies for patterned illumination. In addition, the light source 400 may emit a continuous or pulsed output, and may generate light that is within any desired spectral window of electromagnetic waves.

It should also be appreciated that the light source 400 may also include a light diffuser.

In some embodiments, particularly when it is desired to observe a fluorescence emission spectra from the object being illuminated and observe through the imaging and display system 100, the light source 400 selectively shines through a spectral filter 402 (FIG. 2) that blocks the wavelength of the emission spectra to be observed, such that the light source 400 does not interfere with the observance of that emitted wavelength. For example, if the object is to be observed for fluoresce at a certain wavelength, the spectral filter 402 would be chosen to block that wavelength from the light source so that the light source does not interfere with the observance of the emitted fluorescence. In some such embodiments, the light source is a white light source thus providing a broad spectrum, and the spectral filter is appropriately chosen based on the emission spectra to be observed. In some embodiments, the light source is one or more white light emitting diodes (LED). In some embodiments, the individual light sources are white light emitting diodes (LED) that are filtered by a 775 nm low-pass filter. In another embodiment, the low-pass filter may be replaced with a polarizer, or may be used in conjunction with the filter the light source shines through a spectral filter.

Figure 4:
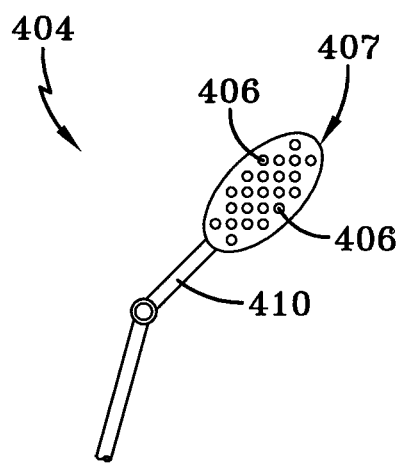
FIG. 4 is a front perspective view of a shadowless surgical light in accordance with an embodiment of this invention.
Figure 5:
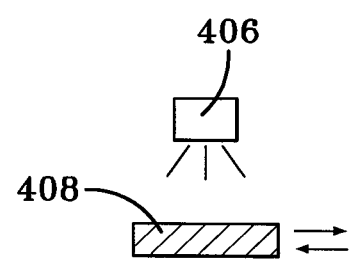
FIG. 5 is a general schematic showing the use of a spectral filter with individual lights of the shadowless surgical light of FIG. 4.

With reference to FIGS. 4 and 5, in another embodiment, the light source 400 may comprise a shadow-less light 404 which is desirable for use during surgery (i.e. a surgical light). The shadow-less light 404 includes a plurality of individual light sources 406 spaced apart in a support 407 to project light onto an object such that a shadow cast by an intervening object and one or more of the plurality of individual light sources is negated by at least one other of the plurality of individual light sources. For example, the shadow-less light 404 can be a surgical light and a surgeon my interpose a hand and arm between the shadow-less light 404 and the patient and thus certain individual light sources would tend to cast a shadow onto the patient but for the fact that other light sources will not have the hand/arm of the surgeon interposed between the shadow-less light source and the surgeon such that those lights will negate the shadow, thus leading to shadow-less lighting. As known, the support 407 is on the end of a swing arm 410, or a goose neck or other connection providing the ability to position the light 404 as desired. This concept of a shadowless light source is separately at invention herein outside of the imaging and display system 100.

In some embodiments, particularly when it is desired to observe an emission spectra from the object, the individual light sources 406 of the shadow-less light 404 selectively shine through a spectral filter 408 (FIG. 5) that blocks the wavelength of the emission spectra to be observed, such that the shadow-less light source does not interfere with the observance of that emitted wavelength. In some embodiments, the individual light sources are white light emitting diodes (LED). In some embodiments, the individual light sources are white light emitting diodes (LED) that are filtered by a 775 nm low-pass filter. In another embodiment, the low-pass filter may be replaced with a polarizer, or may be used in conjunction with the filter.

In a particular embodiment, the light source 400 is a fluorescence-friendly shadow-less surgical light, which can provide white light surgical illumination and florescence illumination without leaking frequencies overlapping with fluorescence emission. This shadow-less light offers both well-rendered surgical illumination (looks like white light to naked light) and fluorescence excitation at the same time. In one embodiment, such light source comprises a plurality of white light emitting diodes (LED) coupled with Notch Filters that are Optical Filters that selectively reject a portion of the spectrum, while transmitting all other wavelengths. With the notch the frequencies overlapping with fluorescence emission, which are emitted by white LEDs, are rejected. It should be appreciated that in some cases edge filters can be used to achieve similar results in blocking the frequencies overlapping with fluorescence emission. In one example, the shadow-less light source comprises a plurality of white light emitting diodes (LED) that is filtered by a 775 nm low-pass filter. It should be appreciated that thin films or other devices may play similar role as notch filters or edge filters in the fluorescence-friendly shadow-less surgical light. In one aspect, the shadow-less light 400 may comprise an array of white lamps with edge filters or notch filters. In another embodiment, the spectral filters may be replaced with polarizers, or may be used in conjunction with the filters.

In some embodiments, the light source is a traditional projector (lamp based) or digital projector (LED-based) selectively used in conjunction with spectral filters or polarizers (as described with other light sources). The projector can also selectively project spatial frequencies (i.e., provide patterned illumination). The spectral filters can be in a filter wheel as already described. The projector beneficially provide a well-defined illumination area. The projector can be set to project any desired wavelength of light and can project without brighter and dimmer areas (i.e., provides consistent light).

Figure 6:
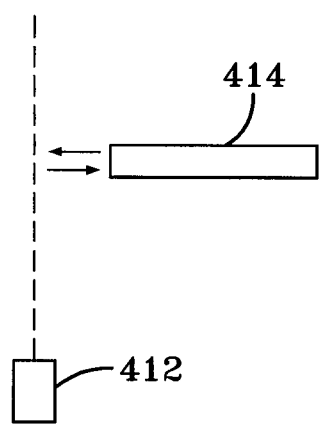
FIG. 6 is a general schematic of a laser and laser diffuser light source, shown with the diffuser out of the path of the laser.
Figure 7:
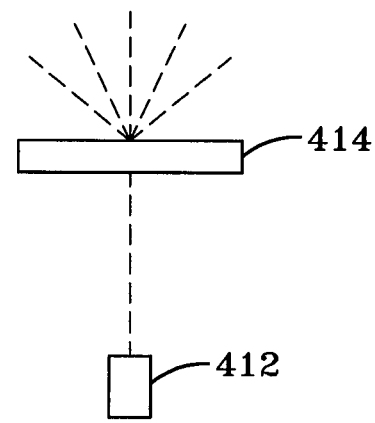
FIG. 7 is a general schematic of a laser and laser diffuser light source, shown with the diffuser in the path of the laser.

With reference to FIGS. 6 and 7, in another embodiment, the light source 400 comprises a laser diode 412 and a diffuser 414 movable to be selectively interposed between the laser diode 412 and the object. Without the diffuser 414 interposed, the laser diode 412 simply shines a focused beam of light, while, with the diffuser 414 interposed, the laser shines over a greater surface area and is suitable for general illumination. In some embodiments this can allow for switching between laser aiming and night vision (with diffuser out of light path) or fluorescence-guided treatment (with diffuser in light path). In addition, the laser diode with diffuser 400 may also use a filter. In addition, the laser diode 400 may also be pulsed, or frequency modulated to reduce the average amount of light energy delivered.

Figure 8:
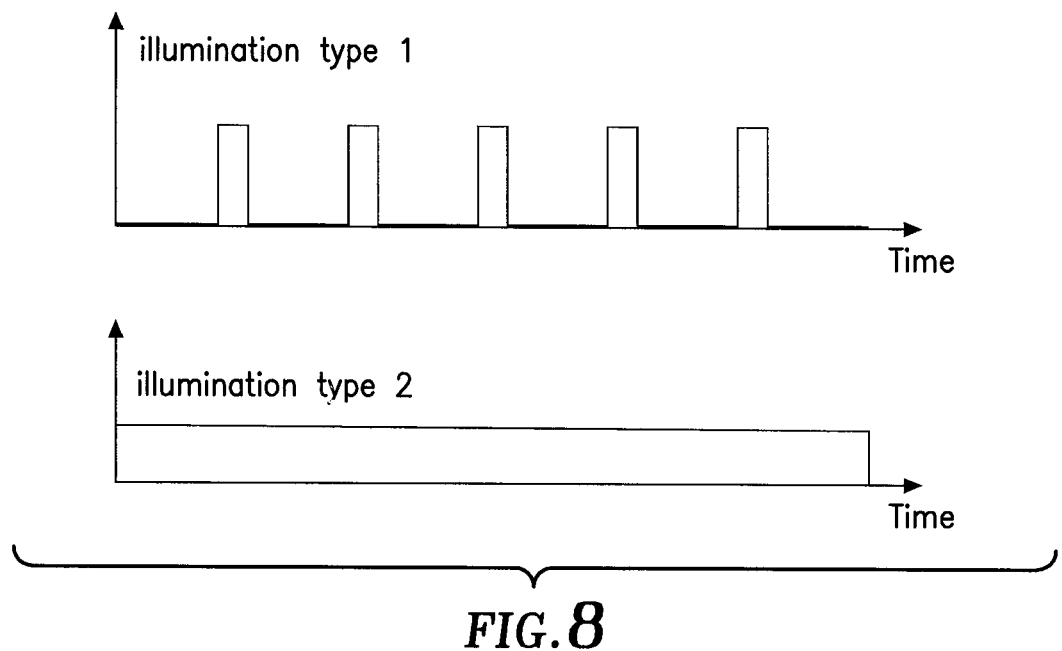
FIG. 8 is a graph showing a plurality of illumination pulse patterns output by a light source for use with the imaging and display system in accordance with the concepts of the present invention.
Figure 9:
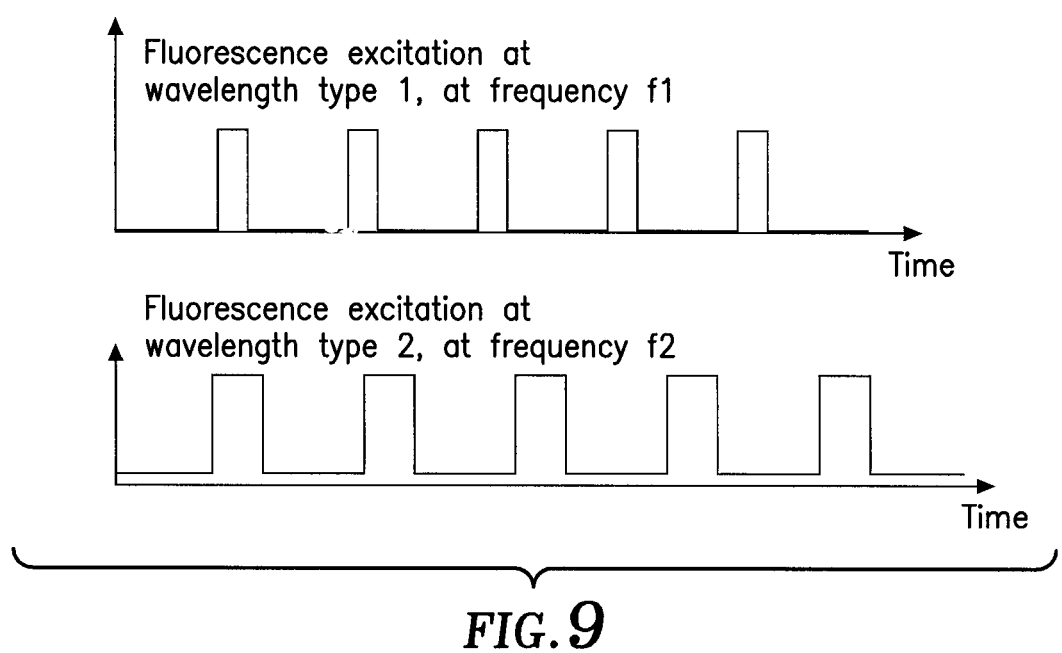
FIG. 9 is a graph showing another plurality of illumination pulse patterns output by the light source in accordance with the concepts of the present invention.

As seen in FIGS. 8 and 9, in some embodiments, the light source 400 may comprise a pulsed light source, or may utilize frequency modulation or pulse-duration modulation. In one aspect, the detector 120 may detect signals of a given frequency or spectrum, and the light source 400 may correlate the detected signal with the frequency modulation and pulse-duration modulation. In one aspect, the light source 400 may modulate the emitted light using an electro-optic modulator, optical chopper, or the like. Alternatively, if the light source 400 comprises one or more light emitting diodes (LED) the light source 400 may operate to adjust the intensity of light being output by adjusting the frequency of the AC (alternating current) that is supplied to power the LEDs.

Specifically, as shown in FIG. 8, the DC component of the light source 400 detected by the goggle system 100 are the fluorescence image type-1, and the AC component of the light detected by the goggle system 100 are florescence image type-2. The goggle system 100 may use a 2-camera setup or a 4-camera setup. The goggle system 100 is configured to detect the signals, correlated with the frequency modulation or pulse-duration modulation. Various ways of modulating the light may be used, such as an electro-optic modulator, an optical chopper, or the like. If LEDs are used, the illumination output by the light source 400 can be modulated by supplying AC current of desirable frequency through the LEDs. A lock-in amplifier may be used by the system 100. It should be appreciated that light bulbs, lamps, laser diodes, lasers or the like could be used instead of LED based light source 400.

Furthermore, as shown in FIG. 9, the frequency component of the light source 400 designated f1, which is detected by the goggle system 100 will be the fluorescence image type-1, and the frequency component of the light designated f2 that is detected by the goggle system 100 is the fluorescence image type-2. The goggle system 100 may use a 2-camera setup or 4-camera setup, and the goggle system 100 will detect the signals, correlated with the frequency modulation or pulse-duration modulation. Possible ways of modulating the light may comprise electro-optic modulator, optical chopper, or the like. In addition, if LEDs are used, the illumination output by the light source 400 can be modulated by supplying AC current of desirable frequency through the LEDs. In addition, a lock-in amplifier may be used by the system 100. It should be appreciated that light bulbs, lamps, laser diodes, lasers or the like could be used instead of LED based light source 400.

It is also contemplated that the system 100 includes a microphone 480 and a speaker 490 to enable verbal communication between the various systems 100A-X and other computer systems (i.e. tablet computers, smart phones, desktop computers), and the like.

Thus, with the structural arrangement of the various components of the multipurpose imaging and display system 100 set forth above, the following discussion will present various embodiments of the system 100 for executing specific functions.

The system 100 may be configured whereby the filter 150 is placed in a first state, such as in military applications, so that it is moved out of the field of view of the detector 120 (i.e. filter not used) to provide night vision imaging of the target 130. Alternatively, the filter 150 may be placed in a second state, such as in medical applications, so that the filter 150 is in the field of view of the detector 120 (i.e. filter is used) to enable fluorescence imaging of the target 130. In addition, any suitable contrast agent, such as indocyanine green (ICG) may be used that is compatible with the frequency spectrum for which the filter 150 is sensitive to facilitate the fluorescence detection enabled by the filter 150. As previously discussed, any suitable filter 150 that is sensitive to a desired spectrum of frequencies may be used so that only the particular targets 130 emitting the desired frequencies are imaged. It should be appreciated that either autofluorescence or extrinsic fluorescence from contrast agents could be detected. In addition, such fluorescence imaging has application in medical applications such as intraoperative imaging, wound assessment, but also in military applications to carry out the detection of biological and chemical warfare.

The system 100, as previously discussed by use the polarizer 152 in a convertible or selective manner, such that when polarization is invoked in a first state, the detector 120 provides polarization-gated imaging, polarization difference imaging, spectral-difference polarization imaging, Muellar matrix imaging for both military and medical applications.

For example, the system 100 may also use traditional division of time techniques, as well as tunable liquid crystal polarization filters or division of focal plane technology (e.g. Moxtek micropolarizer arrays).

As previously discussed, the detector 120 provided by the system 100 may also comprise a thermal imaging sensor, which can be used for both night vision and thermal vision. As such, vascularity, micro-circulation, ischemia can be assessed based on the thermographic images collected by the system 100. In one aspect, the detector 120 may comprise a FLIR Compact A-Series LWIR thermal cameral. In one aspect, the thermal imaging sensor comprising the detector 120 may comprise a cooled infrared image detector or an un-cooled infrared image detector.

The system 100 may also be used to perform hyperspectral imaging for both remote sensing and intelligence gathering in military fields, and various medical applications. Furthermore, such hyperspectral imaging is achieved by using a tunable filter 150 or spectrophotometer employed as a peripheral 350 that is configured to be sensitive to the spectrums being imaged.

It should be appreciated that the system 100 may be configured so that the detector 120 and the filter 150 selected allows near-infrared (NIR), thermal, and hyperspectral imaging to be performed by the same system 100. The selective employment of different peripherals 350 offer additional capabilities to system 100.

The system 100 may also be used to detect biohazard agents, such as viruses, bacteria or any other pathogens or any chemical warfare agents. Tracer or contrast agents may be applied to highlight the biohazard agents. Possible contrast agents include, but are not limited to: fluorescent agents, photosensitizers, nanoparticles, peptides and their conjugates, antibodies and their conjugates, small molecules, and the like.

The signal emitted by the contrast agents (such as fluorescence) can be detected by the system 100. In addition, through employments of different peripherals 350, additional capabilities can be provided to facilitate the biohazard detection. For instance, hyperspectral imaging can be used as a peripheral 350. Devices such as absorption spectrometer, fluorescence spectrometer, diffuse reflectance spectrometer, Raman spectrometer or surface enhance Raman spectrometer can be used as peripherals 350 to provide additional information as appropriate.

It should be appreciated that the system 100 still has the capacity to offer night vision, or medical imaging guidance.

Different imaging or sensing devices may be employed as peripherals 350 to achieve different purposes.

As previously discussed, each imaging and display system 100 includes the detector 150 and a communication interface 250, which allows a plurality of systems 100A-X to communicate various data with one another and/or with one or more remote computing devices. It should be appreciated that the system 100 may be configured to form ad-hoc networks between each one of the individual systems 100A-X, or may be configured to join any exiting wireless communication network, such as a cellular data network, radio-frequency communication, wireless LAN, wireless PAN, WiFi or Bluetooth network for example. As previously discussed, each system 100 has the ability to be a sender of data and a recipient of data. As such, the network of systems 100 may be used for both military/defense and medical purposes.

In one embodiment, the detector 120 of one system 100 may capture image or video data that is transferred over the network to one or more other systems 100A-X or any other computing device (i.e. tablet, computer, smartphone) that are connected to the communication network. Such image transfer may occur simultaneously between the systems 100A-X in real-time or in near real-time. The real-time or near real-time transmission of image or video data, such as viewing an injured person in the field, from one system 100 may be used by recipients of the image or video data at one or more other users of the system 100, or any other users of other computer systems connected to the network, in order to analyze and provide medical guidance to based on the transferred images. In addition, such networked systems 100 allow the point-of-view or field-of-view of the system 100 at which the image originates to be relayed to the other network systems 100, to facilitate medical training, diagnosis, and treatment. As a result, the point of view or field of view of one system 100 can be presented to other networked systems 100 or computing systems.

In addition, the network of systems 100 may also be used to enable the visualization of educational content, including but not limited to medical training, intelligence, and military training and the like.

When the system 100 is configured with a GPS peripheral 350, the system 100 is able to provide navigational information. As such, the system 100 may be able to report the location of the device 100, communicate the location to another remote location over the communication network to which the system 100 is connected. Furthermore, all navigational information can be used by the system 100 to tag all data that is gathered by the system 100, such as images collected for example.

The system 100 may also include microscopic imaging features. In one aspect, the detector 120 may include the necessary optics to provide microscopic imaging. In one aspect, the detector 120 may have built-in optics to conduct microscopic imaging or may have interchangeable optical components for microscopic imaging. In another aspect, the microscope may be provided as a separate peripheral 350 that is coupled to the peripheral interface 300, such that the image supplied by the microscope may be presented on the display or communicated through the network other systems 100 and networked devices, as previously discussed.

The system 100 may also be utilized to facilitate telemedicine functions. For example, the system 100 allows a surgeon in remote areas to perform surgery under the supervision of an expert surgeon. The system 100 can also assist combat medics to perform procedures under the remote guidance of a clinician. Additionally, the system 100 can also load the location-specific patient/military information to another site where the data can be stored and organized; the system 100 can upload patient information for data storage, medical record keeping, diagnosis, telemedical consultation, epidemic tracking and epidemiology. Other systems 100 may communicate via the network simultaneously.

A central networked computer unit may maintain a database of all records, such as medical records, from where reminders can be sent to clinician/technicians for point-of-care check-up or follow-up with patients. In one embodiment, the system 100 can enable telesurgery where a remote medical clinician may control a local surgical-robot using the network to perform surgery from a remote site.

It should also be appreciated that the system 100 may be used achieve a variety of functions using the imaging, display, and collaborative communications features of the present invention. As such, the following discussion presents a variety of applications demonstrating the beneficial aspects of convertible operating mode provided by the system 100, whereby examples are provided in which the system 100 is placed in a military operating mode or a medical operating mode. Moreover, while the examples are descriptive of a variety of applications of the system 100, such examples are not limiting. In particular, the system 100 may be used to image, monitor and treat injuries and wounds using the collaboration between a user of the system and remote medically-trained personnel that are in collaborative communication with each other. Similarly, the system 100 may also be used to perform medical interventions with limited resources/military constraints before evacuation, and to guide and enable first-responders to perform medical tasks, including surgeries, and wound debridement. The ability for multiple users of the system 100 to collaborate also allows the users to provide medical assistance and advisement to one another. Additionally, the system 100 allows the users to guide a triage of large numbers of casualties, as well as staged treatment in the field; enable telemedicine that allows for 2-way telemedical collaboration between first responders and medical advisors; enable remote triage, monitoring and management of casualties, aided by experts; provide medical decision support with automated algorithms in conjunction with telemedical advisement from a remote site; guide treatment of hemorrhage, detection of vascular collapse and significant tissue damage due to perfusion deficits; facilitate diagnosis of brain and spinal cord injury; monitor and guide treatment to reduce secondary damage such as ischemia/perfusion injury after trauma; offer guidance to decontaminate, debride, protect and stabilize hard and soft tissue wounds; offer diagnostic and prognostic algorithms for non-medical and medical professionals; guide the assessment and treatment of dental injuries; guide the assessment and treatment of maxillofacial trauma repair, as well as orthopedic injuries.

It should also be appreciated that the system 100 may be used to facilitate medical biological defense; provide medical countermeasures for biological warfare agents; guide prophylaxis and pretreatment to prevent casualties; to allow the identification and diagnosis of biological agents, such as infectious agents including, but not limited to: anthrax, plague, Glanders, Ebola, and Marburg viruses, as well as the Venezuelan, western and eastern equine encephalitis viruses; and the poxvirus models of variola virus. Examples of toxins detectable by the system 100 may include those derived from plants, such as Ricin, and those derived from bacteria, such as staphylococcal enterotoxins and botulinum.

The system 100 may also be used to facilitate medical chemical defense; provide diagnostic and prognostic indicators for chemical warfare agent casualties; and provide detection of chemical agents that may include vesicant or blister agents (e.g. sulfur mustard), blood agents (e.g. cyanide), respiratory agents (e.g. phosgene) and nerve agents (e.g. GA or Tabun, GB or Sarin, GD or Soman, and VX).

In addition, the system 100 may also be used to characterize the mechanisms of vesicant agent pathology to identify medical countermeasures against vesicant agents; provide rapid and accurate analysis of human tissues and body fluids for detection of chemical warfare agent exposures.

The system 100 is also configured to serve as a training platform for military and medical purposes, whereby the system 100 utilizes augmented reality/virtual reality for training procedures and for combat casualty training for soldiers and combat medics.

Furthermore, the system 100 also provides biomonitoring and telemedical assistance in hospitals, the home and in the field.

In addition, the system 100 may also be integrated with medical robots and telesurgical applications.

In one aspect, the memory unit of the system 100 may store software to simulate a medical or military training procedure that is based on virtual reality or augmented reality. Two dimensional or three dimensional images or video may be stored at the memory unit of the system 100, or in a remote server coupled to the network to which the system 100 is connected, which enables visualization of educational content, such as medical training, intelligence training, and military training.

In another aspect, the training software may include audio-visual training tutorials with step-by-step instructions for carrying out particular procedures via the display 110. In addition, the tutorials may outline tasks for how to prepare for an examination, how to operate ultrasound, and how to position a patient. Ultrasound techniques, such as how to manipulate the ultrasound probe and use the keyboard functions of the ultrasound system may be included. The tutorials may also include various examination protocols; reference anatomy information with reference ultrasound images; procedures for how to make a diagnosis; and procedures for how to treat patients and treatment tutorials may be included. With networked systems 100, the training can be augmented by having educators networked in by having their own system 100 to interact with students with their own system 100. This is particularly adapted to use of a goggle system 100.

In another embodiment, the system 100 may be used to detect blood or any other target 130 based on intrinsic absorption, auto-fluorescence, or extrinsic fluorescence and chemiluminescence. In one aspect, a mixture of predetermined fluorescence tracers, such as Hemascein for example, may be used to spray an area or region being investigated, which reacts with a desired target of interest 130 to cause the target 130 to fluoresce so as to be detected by the system 100, as previously discussed. In this case, a 475 nm bandpass filter 150 may be used with the Hemascein to detect blood as the target of interest (TOI) 130 using the system. It should be appreciated that the system 100 may be used to detect other forensic evidence. The networking feature of system 100 may be used as appropriate to enable communication between systems 100A-X.

In addition, through employments of different peripherals 350, additional capabilities can be provided to facilitate the forensic detection. For instance, hyperspectral imaging can be used as a peripheral 350. Devices such as absorption spectrometer, fluorescence spectrometer, diffuse reflectance spectrometer, Raman spectrometer or surface enhance Raman spectrometer can be used as peripherals 350 to provide additional information as appropriate.

It should be appreciated that the system 100 still has the capacity to offer night vision. Different imaging or sensing devices may be employed as peripherals 350 to achieve different purposes.

In one aspect, the light source 400 may have components that overlap with emission spectra, referred to as bleed-through components. The bleed-through components can be tunable to achieve desirable level of background. For example, in the case of indocyanine green dye, if the emission filter is an 820 nm long-pass filter, the component of illumination is >820 nm will pass through the emission filter (if emission filter is 820 nm long pass filter) and become the background, or the bleed-through component. The illumination could have both 780 nm LEDs for fluorescence excitation and 830 nm LEDs for bleed-through. By changing the intensity of the 830 nm LEDs, the level of background can be adjusted, which is useful in a variety of situations.

Based on the foregoing, the advantages of the present invention are readily apparent. The main advantage of this invention is to provide a convertible system, which has application in both military and medical fields. Still another advantage of the present invention is that medical applications can be enabled in part based on existing defense technology platforms. Yet another advantage of the present invention is that only one system is needed for use in both military and medical fields, such that same equipment used for military uses can be used to provide enhanced medical care, without increasing the amount of equipment needed. Still another advantage of the present invention is that diverse tasks can be performed with one system, such as to diagnose, monitor, provide wound treatment, identify infectious diseases and spinal cord/brain injury, and the like. Another advantage of the present invention is that triage and treatment can be guided with automated mechanism and/or remote telemedical guidance, such that treatment from non-medical professionals can be facilitated. An additional advantage of the present invention is that countermeasures against biological and chemical warfare can be facilitated within the system without additional equipment. Still another advantage of the present invention is that first responders can use the system to perform complex tasks, provide self-aid and aid to others, while empowering medical personnel to do more within military constraints. Another advantage of the present invention is that the system is lightweight, easily transportable, battery-operated and self-contained. Yet another advantage of the present invention is that the system provides microscopic imaging capability. An other advantage of the present invention is that GPS and remote communication are provided by the system to facilitate warfare and medical management.

Thus, it can be seen that the objects of the present invention have been satisfied by the structure and its method for use presented above. While in accordance with the Patent Statutes, only the best mode and preferred embodiment has been presented and described in detail, it is to be understood that the present invention is not limited thereto or thereby. Accordingly, for an appreciation of the true scope and breadth of the invention, reference should be made to the following claims.

What is claimed is:

1. A system for capturing images of a target of interest associated with a patient in real-time and simultaneously displaying the captured images in real-time to a user that is engaging the target of interest associated with the patient, comprising:
- a wearable display that is worn on a head of the user as the user engages the target of interest associated with the patient and is configured to display in real-time a portion field of view to the user as the user engages the target of interest associated with the patient via the wearable display simultaneously as images of the target of interest associated with the patient are captured and streamed in real-time to the wearable display, wherein the portion field of view that is thereby displayed to the user by the wearable display is less than a total field of view of the user;
- a detector that is coupled to the wearable display and is configured to capture an imaging field of view of the target of interest associated with the patient in real-time as the user engages the target of interest associated with the patient, wherein real-time is when the imaging field of view of the target of interest associated with the patient is captured as the user engages the target of interest associated with the patient thereby enabling the user to view the portion field of view simultaneously as the detector is capturing the imaging field of view;
- a filter configured to filter image data of the imaging field of view of the target of interest as captured by the detector to image data that is within a first frequency spectrum; and
- a computing device configured to:
  - select a portion field of view level from a plurality of portion field of view levels that the image data is to be filtered from the imaging field of view of the target of interest associated with the patient that is within the selected field of view level,
  - filter image data from the imaging field of view of the target of interest associated with the patient that is included in the selected portion field of view level as the detector captures the imaging field of view of the target of interest associated with the patient in real-time,
  - adjust the imaging field of view of the target of interest associated with the patient as captured by the detector in real-time to the selected portion field of view level of the target of interest associated with the patient thereby adjusting the image data that is filtered from the imaging field of view of the target of interest associated with the patient to that is within the selected portion field of view level as displayed to the user by the wearable display based on the filtered image data as included in the selected portion field of view level, and
  - instruct the wearable display to display in real-time to the user the selected portion field of view level based on the filtered image data simultaneously as the detector is capturing the imaging field of view as the user engages the target of interest associated with the patient, wherein the selected portion field of view level that is thereby displayed to the user by the wearable display is less than the total field of view of the user.

2. The system of claim 1, wherein the computing device is further configured to:
- filter image data from the imaging field of view of the target of interest that is within a zoom level associated with a zoom field of view, wherein the zoom level indicates the image data that is to be filtered from the imaging field of view to generate the zoom field of view that encompasses image data that is within the zoom level;
- adjust the imaging field of view of the target of interest as captured by the detector to the zoom level field of view of the target of interest based on the filtered image data that is within the zoom level; and
- instruct the wearable display to display to the user the zoom level field of view that is thereby displayed to the user by the wearable display, wherein the zoom level field of view is less than the imaging field of view of the detector.

3. The system of claim 2, wherein the computing device is further configured to:
- select a zoom level from a plurality of zoom levels that image data is to be filtered from the imaging field of view of the target of interest that is within the selected zoom level; and
- adjust the zoom level to the selected zoom level thereby adjusting the image data that is filtered from the imaging field of view of the target of interest that is within the selected zoom level.

4. The system of claim 1, wherein the computing device is further configured to:
- filter image data from the imaging field of view of the target of interest that is within a resolution associated with a resolution field of view, wherein the resolution indicates the image data is to be filtered from the imaging field of view to generate the resolution field of view that encompasses image data that is within the resolution;
- adjust the imaging field of view of the target of interest as captured by the detector to the resolution field of view of the target of interest based on the filtered image data that is within the resolution; and
- instruct the wearable display to display to the user the resolution field of view that is thereby displayed to the user by the wearable display, wherein the resolution field of view is less than the imaging field of view of the detector.

5. The system of claim 4, wherein the computing device is further configured to:
- select a resolution from a plurality of resolutions that image data is to be filtered from the imaging field of view of the target of interest that is within the selected resolution; and
- adjust the resolution to the selected resolutions, thereby adjusting the image data that is filtered from the imaging field of view of the target of interest that is within the selected resolution.

6. The system of claim 1, wherein the computing device is further configured to:
- filter image data from the imaging field of view of the target of interest that is within a working distance associated with a working distance field of view, wherein the working distance indicates the image data that is to be filtered from the imaging field of view to generate the working distance field of view that encompasses image data that is within the working distance;
- adjust the imaging field of view of the target of interest as captured by the detector to the working distance field of view of the target of interest based on the filtered image data that is within the working distance; and
- instruct the wearable display to display to the user the working distance field of view that is thereby displayed to the user by the wearable display, wherein the working distance field of view is less than the imaging field of view of the detector.

7. The system of claim 6, wherein the computing device is further configured to:
select a working distance from a plurality of working distances that image data is to be filtered from the imaging field of view of the target of interest that is within the selected working distance; and
adjust the working distance to the selected working distance thereby adjusting the image data that is filtered from the imaging field of view of the target of interest that is within the selected working distance.

8. The system of claim 1, wherein the detector is further configured to:
capture image data from the imaging field of view of the target of interest that is within the first frequency spectrum as filtered by the filter.

9. The system of claim 8, wherein the first frequency spectrum is a near infrared frequency.

10. The system of claim 1, further comprising:
a light source that includes a plurality of individual light sources with each individual light source spaced a part from each other individual light source and is configured to project light onto the target of interest and prevent a shadow cast by an intervening object onto the target of interest due to the spacing of the individual light sources.

11. The system of claim 10, further comprising:
a plurality of Light Emitting Diodes (LEDs) as the plurality of light sources with each LED spaced apart from each other individual light source and is configured to emit white light; and
a spectral filter that is positioned so that the white light emitted by the LEDs is propagated through the spectral filter and is configured to block a wavelength of an emission spectra that the image is to be displayed to the user to prevent the white light emitted by the LEDs from interfering with an observance of the emitted wavelength by the user as the image is displayed to the user.

12. The system of claim 1, wherein the detector is a three-dimensional camera.

13. The system of claim 1, further comprising:
a peripheral interface configured to communicate with at least one peripheral, wherein the at least one peripheral is a robot.

14. A system for capturing images of a target of interest associated with a patient in real-time and simultaneously displaying the captured images in real-time to a user that is engaging the target of interest associated with the patient, comprising:
a wearable display that is worn on a head of the user as the user engages the target of interest associated with the patient and is configured to display in real-time a zoom level associated with a zoom field of view to the user as the user engages the target of interest associated with the patient via the wearable display simultaneously as images of the target of interest associated with the patient are captured and streamed in real-time to the wearable display, wherein the zoom level associated with the zoom field of view that is thereby displayed to the user by the wearable display is less than a total field of view of the user;
a detector that is coupled to the wearable display and is configured to capture an imaging field of view of the target of interest associated with the patient in real-time as the user engages the target of interest associated with the patient, wherein real-time is when the imaging field of view of the target of interest associated with the patient is captured as the user engages the target of interest associated with the patient thereby enabling the user to view the zoom level associated with the zoom field of view as the detector is capturing the imaging field of view;
a filter configured to filter image data of the imaging field of view of the target of interest as captured by the detector to image data that is within a first frequency spectrum, wherein the first frequency spectrum includes color image data; and
a computing device configured to:
filter the color image data from the imaging field of view of the target of interest that is within the zoom level associated with the zoom field of view, wherein the zoom level indicates the color image data that is to be filtered from the imaging field of view to generate the zoom field of view that encompasses color image data that is within the zoom level;
adjust the imaging field of view of the target of interest as captured by the detector to the zoom field of view of the target of interest based on the filtered color image data that is within the zoom level; and
instruct the wearable display to display to the user the zoom level field of view that is thereby displayed to the user by the wearable display, wherein the zoom level field of view is less than the imaging field of view of the detector.

15. The system of claim 14, wherein the computing device is further configured to:
select a zoom level from a plurality of zoom levels that image data is to be filtered from the imaging field of view of the target of interest that is within the selected zoom level; and
adjust the zoom level to the selected zoom level thereby adjusting the image data that is filtered from the imaging field of view of the target of interest that is within the selected zoom level.

16. A system for capturing images of a target of interest associated with a patient in real-time and simultaneously displaying the captured images in real-time to a user that is engaging the target of interest associated with the patient, comprising:
a wearable display that is worn on a head of the user as the user engages the target of interest associated with the patient and is configured to display in real-time a resolution associated with a resolution field of view to the user as the user engages the target of interest associated with the patient via the wearable display simultaneously as the images of the target of interest associated with the patient are captured and streamed in real-time to the wearable display, wherein the resolution associated with the resolution field of view that is thereby displayed to the user by the wearable display is less than a total field of view of the user;
a detector that is coupled to the wearable display and is configured to capture an imaging field of view of the target of interest associated with the patient in real-time as the user engages the target of interest associated with the patient, wherein real-time is when the imaging field of view of the target of interest associated with the patient is captured as the user engages the target of interest associated with the patient thereby enabling the user to view the resolution associated with the resolution field of view as the detector is capturing the imaging field of view;

a filter configured to filter image data of the imaging field of view of the target of interest as captured by the detector to image data that is within a first frequency spectrum, wherein the first frequency spectrum includes fluorescence image data; and a computing device configured to:
  filter the fluorescence image data from the imaging field of view of the target of interest that is within a resolution associated with a resolution field of view, wherein the resolution indicates the fluorescence image data is to be filtered from the imaging field of view to generate the resolution field of view that encompasses fluorescence image data that is within the resolution;
  adjust the imaging field of view of the target of interest as captured by the detector to the resolution field of view of the target of interest based on the filtered fluorescence image data that is within the resolution; and
  instruct the wearable display to the user the resolution field of view that is thereby displayed to the user by the wearable display, wherein the resolution field of view is less than the imaging field of view of the detector.

17. The system of claim 16, wherein the computing device is further configured to:
  select a resolution from a plurality of resolutions that image data is to be filtered from the imaging field of view of the target of interest that is within the selected resolution; and
  adjust the resolution to the selected resolution thereby adjusting the image data that is filtered from the imaging field of view of the target of interest that is within the selected resolution.

* * * * *